United States Patent [19]
Malchesky

[11] Patent Number: 5,759,490
[45] Date of Patent: Jun. 2, 1998

[54] POROUS CLIP FOR CONCURRENT CATHETER STERILIZATION AND RESHAPING

[75] Inventor: Paul S. Malchesky, Painesville Township, Ohio

[73] Assignee: Steris Corporation, Mentor, Ohio

[21] Appl. No.: 662,663

[22] Filed: Jun. 14, 1996

[51] Int. Cl.⁶ ........................................................ A61L 2/00
[52] U.S. Cl. ........................... 422/28; 285/422; 422/1; 422/292; 422/293; 422/297; 422/300
[58] Field of Search ........................ 422/1, 26, 28, 422/292, 297, 300, 293; 285/422

[56] References Cited

U.S. PATENT DOCUMENTS

| | | | |
|---|---|---|---|
| 3,839,841 | 10/1974 | Amplatz | 53/21 |
| 4,135,868 | 1/1979 | Schainholz | 422/310 |
| 4,763,678 | 8/1988 | Oh | 422/300 X |
| 4,798,292 | 1/1989 | Hauze | 206/439 |
| 4,799,474 | 1/1989 | Ueda | 128/4 |
| 5,077,008 | 12/1991 | Kralovic et al. | 422/37 |
| 5,084,251 | 1/1992 | Thomas | 422/300 |
| 5,091,343 | 2/1992 | Schneider et al. | 422/297 |
| 5,209,909 | 5/1993 | Siegel et al. | 422/292 |
| 5,310,524 | 5/1994 | Campbell et al. | 422/33 |
| 5,497,601 | 3/1996 | Gonzalez | 53/449 |
| 5,552,115 | 9/1996 | Malchesky | 422/28 |

FOREIGN PATENT DOCUMENTS

0397352 A2  11/1990  European Pat. Off. .

OTHER PUBLICATIONS

"Porex Porous Plastics High Performance Materials", Porex Technologies Advertising Brochure No Date Available.
1994 Bard Resource Book, effective Mar. 1994, pp. 1–16.
"Disinfection and Sterilization", McCulloch, 1945, pp. 91–93.
Steris Corporation Advertising Brochure, 1992.

*Primary Examiner*—Krisanne Thornton
*Attorney, Agent, or Firm*—Fay, Sharpe, Beall, Fagan, Minnich & McKee

[57] ABSTRACT

A countertop decontamination unit (A) has a decontamination chamber (10) which contains items to be sterilized, disinfected, or otherwise microbially decontaminated. A catheter (60) has an initial curve shape (62A). However, the catheter (60) is straightened in use and returns to a shape (62B). During a decontamination cycle, one or more porous clips (64) are disposed into frictional contact with the catheter. The clip (64) holds the catheter in the initial or undersized shape (62A) during the decontamination process. In the decontamination process, the decontamination fluid is heated at least to a temperature that resets the shape memory of the catheter (e.g., 40°–60° C.). The clip (64) has a sufficient porosity that microbial decontamination fluid penetrates through the clip to wet portions of the item surface in frictional contact with the clip assuring total microbial decontamination of the catheter. Once the decontamination is complete and the catheter is cooled, it holds the reset initial shape (62A).

19 Claims, 5 Drawing Sheets

POROUS CLIP FOR CONCURRENT CATHETER STERILIZATION AND RESHAPING

BACKGROUND OF THE INVENTION

The present invention relates to the decontamination art. It finds particular application in conjunction with sterilizing instruments and equipment which contain or potentially contain biological contaminants, such as medical, dental, veterinary, and mortuary instruments and equipment and will be described with particular reference thereto. It is to be appreciated, however, that the invention is also applicable to a wide variety of technologies in which contamination removing or other treating reagents in liquid, gas, or vapor form are blocked by surfaces, connectors, or other treating agent impermeable structures from reaching adjacent surfaces.

Heretofore, medical, dental, and surgical equipment and instruments have often been sterilized in a steam autoclave. Autoclaves kill life forms with a combination of high temperature and pressure. However, steam autoclaves have several drawbacks. The high temperature pressure vessels tend to be bulky and heavy. The high temperature and pressure are unsuitable for endoscopes, rubber and plastic devices, lenses, bearings, portions of devices made of polymeric materials, and the like. Moreover, the autoclave sterilizing and cool down cycle is sufficiently long, that multiple sets of the medical, dental, or surgical instruments are commonly required.

Instruments which cannot withstand the pressure or temperature of the oven autoclave are often sterilized with ethylene oxide gas, particularly in larger medical facilities or hospitals. However, the ethylene oxide sterilization technique also has several drawbacks. First, the ethylene oxide sterilization cycle is even longer than the steam autoclave cycle. The ethylene oxide sterilizing and degassing cycle is sufficiently long that multiple sets of instruments are commonly required. Another drawback is that ethylene oxide sterilization is sufficiently sophisticated that trained technicians are commonly required, making it unsuitable for physician and dental offices and for most smaller medical facilities.

Anti-microbial liquid disinfection systems have also been utilized for equipment which could not withstand the high temperatures of steam sterilization or long cycle times of ethylene oxide. Commonly, a technician mixes a liquid disinfectant composition and manually immerses the items to be decontaminated. The high degree of manual labor introduces numerous uncontrolled and unreported variables into the disinfection process.

Liquid and gaseous anti-microbial systems can kill microbes on all surfaces that the anti-microbial fluid, liquid, or gas can reach. When a contaminated surface engages another surface, there is a potential for a portion of the surface to be shielded from the antimicrobial fluid, liquid, or gas.

Coronary guide catheters are used in interventional procedures in cardiology to gain access to the interior of arteries. The shape and resiliency of these catheters are important to the success of a procedure. The catheters serve as a supporting access pathway for introducing various interventional devices into the coronary vasculature. Depending on its purpose, a catheter's plastic body is designed with various shapes and curves and has a particular stiffness to maintain the curve shape.

In use, a stiff wire is inserted into the catheter to straighten it. The catheter is inserted in its straightened condition with the wire through an artery to the appropriate position in a patient. Once positioned, the stiff wire is carefully slid out. The memory of the plastic causes the catheter to bend back substantially to its original curve shape. Through careful positioning and selection of the catheter's relaxed shape, the inserted end is caused to curve around bends, into branching arteries and into other portions of the vasculature that are otherwise inaccessible to the inserted device. Each time the catheter is straightened, the plastic relaxes and does not return completely to its pre-straightened shape. Even though the plastic memory is typically better than 95% accurate in returning the catheter to its pre-straightened shape, the delicate nature of the medical procedures cannot tolerate many straightening/return cycles. For assured safety, many of these catheters are discarded after a single use.

The present invention provides a new and improved method and apparatus which eliminates the potential for non-fluid contact during decontamination and reshapes plastic instruments.

SUMMARY OF THE INVENTION

In accordance with one aspect of the present invention, a catheter is concurrently microbially decontaminated and reshaped, more specifically, has its plastic memory reset.

In accordance with a more limited aspect of the present invention, at least one porous holding member is placed into frictional contact with the catheter at surface points which maintain the catheter into a desired shape. A microbial decontamination fluid is warmed and circulated to decontaminate the catheter. The porous holding member has a sufficient porosity such that the microbial decontamination fluid penetrates through the porous holding member to the frictionally contacted surface points which assures microbial decontamination of the entire catheter. The fluid is warmed to a temperature effective to reset the plastic memory. After a cooling period, the porous holding member is removed from the catheter and the catheter is substantially reshaped into the desired shape.

In accordance with another aspect of the present invention, a porous clip is provided. The clip includes a porous member which holds a curved plastic item by frictional contact in a pre-selected shape. The porous member has a porosity sufficient to allow a decontamination fluid to flow therethrough to contact all surfaces of the curved plastic item.

One advantage of the present invention is that it permits sterilant and disinfectant contact with medical instrument surfaces in contact with the clip to sterilize or disinfect all surfaces.

Another advantage of the present invention is that it concurrently resets the plastic memory of catheters or other plastic devices during a decontamination cycle.

Another advantage of the present invention is that it enables catheters to be reused safely.

Still further advantages of the present invention will become apparent to those of ordinary skill in the art on reading and understanding the following detailed description of the preferred embodiments.

BRIEF DESCRIPTION OF THE DRAWINGS

The invention may take form in various components and arrangements of components, and in various steps and arrangements of steps. The drawings are only for purposes

DETAILED DESCRIPTION OF THE PREFERRED EMBODIMENTS

Figure 1:
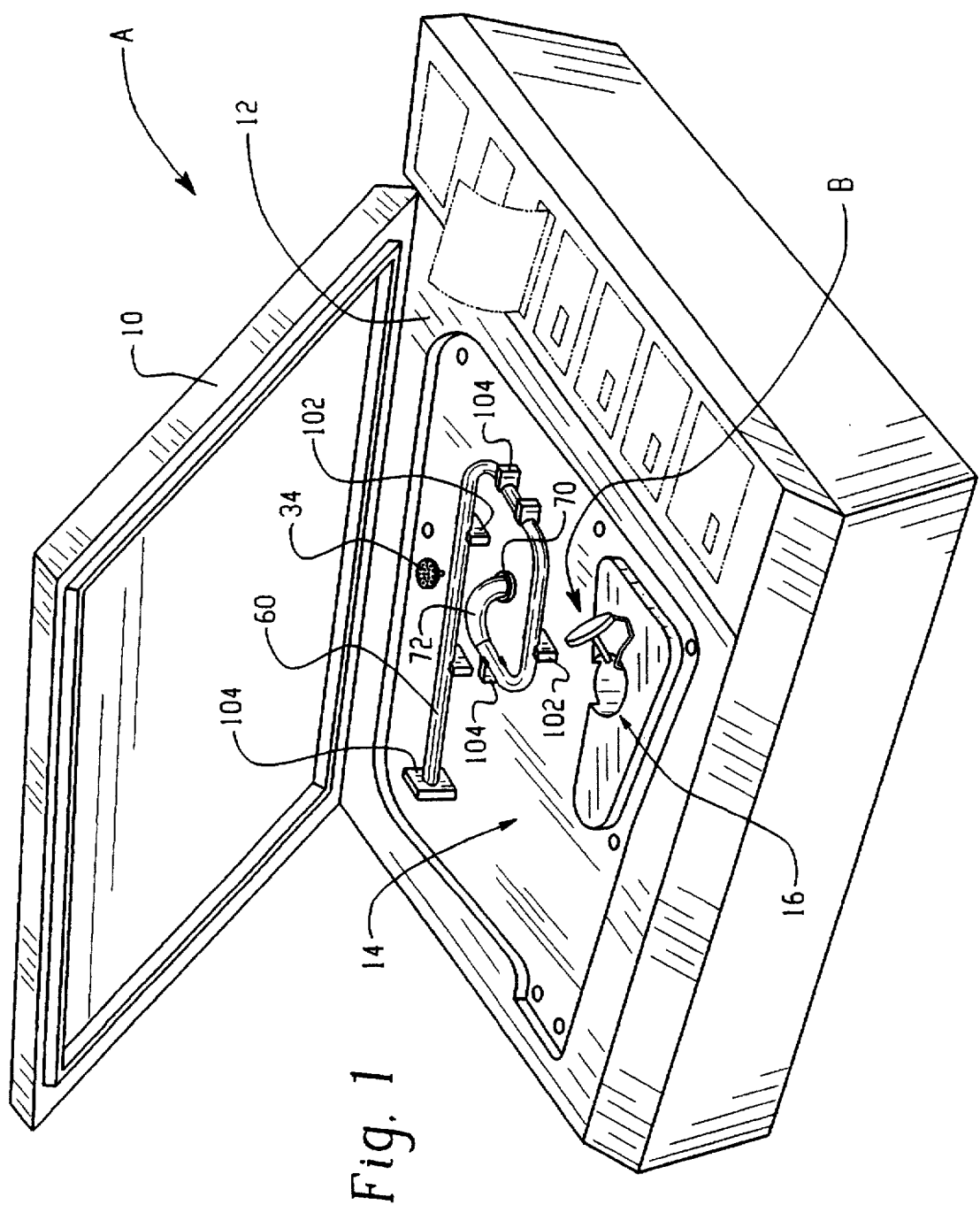
FIG. 1 is a perspective view of a decontamination unit with its door open.

With reference to FIG. 1, a microbial decontamination apparatus A is configured to sit on a countertop or other convenient work surface. A door or lid 10 is manually openable to provide access to a tray 12 which defines a receiving region 14 for receiving items to be microbially decontaminated. Various trays with item receiving regions configured to receive the items themselves or item holding containers are also contemplated. A well 16 receives a unit dose of reagents for forming a sterilant, disinfectant, or other microbial decontaminating solution.

Figure 2:
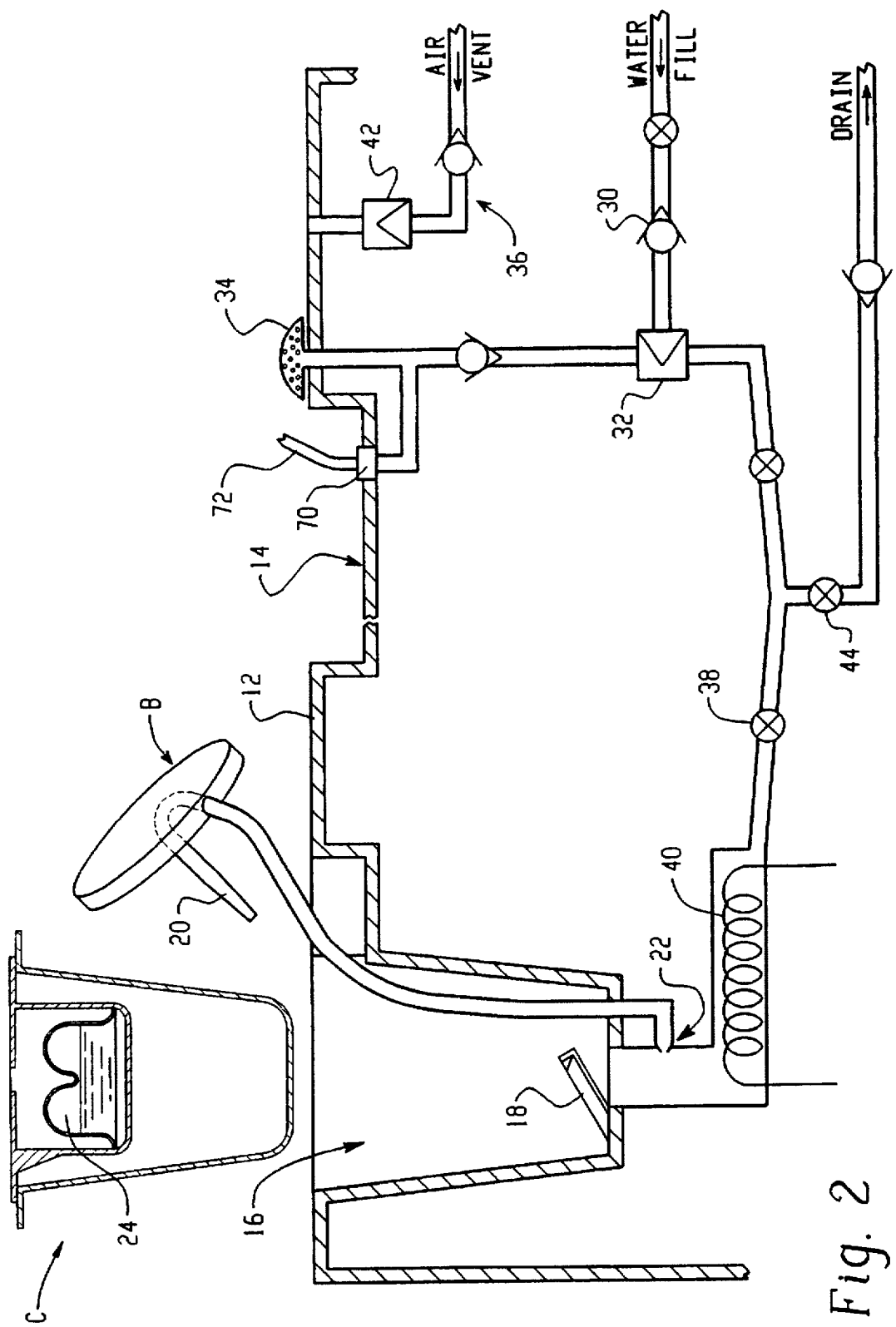
FIG. 2 is a plumbing diagram of the decontamination unit of FIG. 1.

With particular reference to FIG. 2, a reagent containing package C is inserted into the well 16 as a cutter 18 opens the bottom to release buffers and other powdered reagents. Once the items are loaded into the tray and the reagent carrying package C is inserted into the well 16, an aspirator B is inserted into the package. An aspirator tube 20, which is connected with a venturi 22, is inserted into a liquid reagent reservoir 24. After the lid 10 is closed and latched, a fill valve 30 passes water through a microbe removing filter 32 in flow path of a fluid circulating system. The microbe removing filter 32 provides a source of sterile water by passing water and blocking the passage of all particles the size of microbes and larger. The incoming water which has been sterilized by the filter 32 passes through a spray or distribution nozzle 34 and fills the item receiving region 14 in the tray 12. As additional water is received, it flows into the well 16 dissolving powdered reagents in the cup C which has been opened forming an anti-microbial solution. Filling is continued until all air is forced through an air system 36 and an entire interior volume is filled with the sterile water. After the fill valve 30 is closed, a pump 38 circulates the fluid through the venturi 22 aspirating the liquid reagent into the water, as well as through a heater 40, the item receiving region 14 of the tray 12, and the well 16. The heater heats the fluid to about 40°–60° C., with 50°–60° C. being preferred. The pump also passes the anti-microbial solution into and out of the downside side of the filters within the fluid pathway. After the anti-microbial solution has been brought up to temperature and circulated for a selected duration, a drain valve 44 is opened, allowing the solution to drain. Air is drawn through the microbe filter 42 such that sterile air replaces the fluid within the system. Thereafter, the drain valve is closed and the fill valve 30 opened again to fill the system with a sterile rinse fluid. It will be noted, that because the pump 38 circulated the anti-microbial solution over all surfaces of the flow paths including all surfaces leading from the sterile rinse source 32, the rinse cannot bring microbial contaminants into the item receiving region 14.

In the preferred embodiment, the outer cup contains corrosion inhibitors, buffers, and wetting agents. Preferred copper and brass corrosion inhibitors include azoles, benzoates, other five-membered ring compounds, benzotriazoles, tolytriazoles, mercaptobenzathiazole, and the like. Other anti-corrosive buffering compounds include phosphates, molybdates, chromates, dichromates, tungstates, vanadates, other borates, and combinations thereof. These compounds are effective for inhibiting steel and aluminum corrosion. For hard water in which calcium and magnesium salts may tend to precipitate, a sequestering agent such as sodium hexametaphosphate or EDTA may be is also included. The liquid reagent is peracetic acid. Other formulations can be utilized to generate chloride gas, hydrogen peroxide, hypochlorous acid, and other strong oxidants and agents which have a biocidal effect. Suitable anti-microbial fluids also include gases such as ethylene oxide, hydrogen peroxide or peracetic acid vapors, gas plasmas, steam, and the like.

In this manner, the sterilant or other anti-microbial solution sterilizes or microbially decontaminates the rinse fluid sterilizing filter and all paths, passageways, and surfaces downstream from the filter 34. This sterilization of all surfaces prevents sterile rinse fluid from flowing over any surface which was not sterilized or microbially decontaminated during the sterilizing or anti-microbial portion of the cycle.

Figure 3:
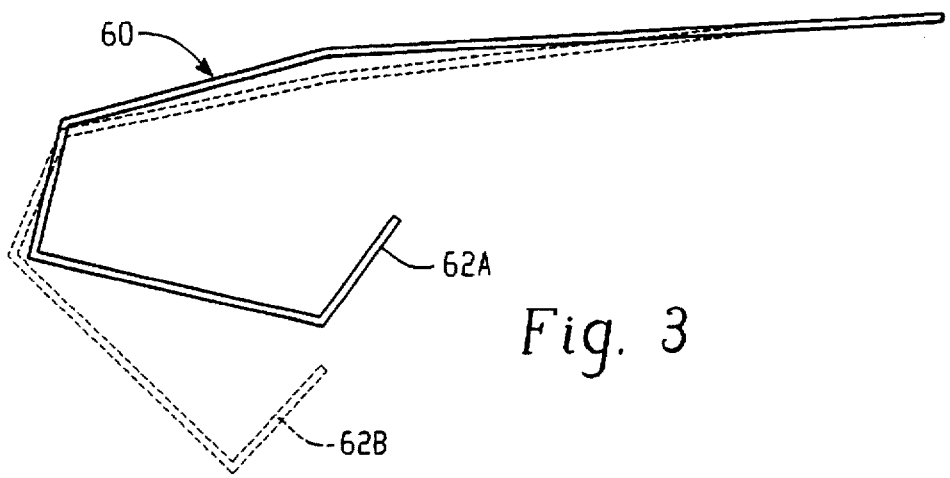
FIG. 3 is an illustration of a catheter in an original shape and in a stretched shape.

With reference to FIG. 3, a catheter 60 having an initial curve shape 62A is constructed of a plastic material. The catheter is shaped with various bends and curves to fit an artery or portion of the vasculature of a patient undergoing surgery. As is the nature of plastic, each time it is flexed, the catheter returns less than fully to its original shape. After the plastic catheter 60 is opened to a straight, linear configuration and then released, it relaxes to a less curved configuration, for example as shown by curve shape 62B.

The catheters are constructed of a plastic polymer that is substantially elastic, i.e., after deformation, it returns almost to its original shape. During manufacture, the plastic catheter is initially formed under a combination of heat and pressure. Under these conditions, the polymer chains intersect physically and chemically to take the shape 62A. The plastic holds shape 62A until it is deformed. During deformation, the relationship among the polymer chains is altered. For example, coiled chains stretch, polymer chains move relative to each other, bonds are broken, chains partially unlink, or the like. When the deformation stops, the alterations cause the catheter to return only to shape 62B. When the plastic is reheated to 50°–56° C., in the preferred embodiment, the plastic "softens", i.e., enables physical and chemical relationships among the polymer chains to be reestablished. Of course, other materials with a heat reset shape memory, such as memory metals, are also contemplated.

Figure 4A:
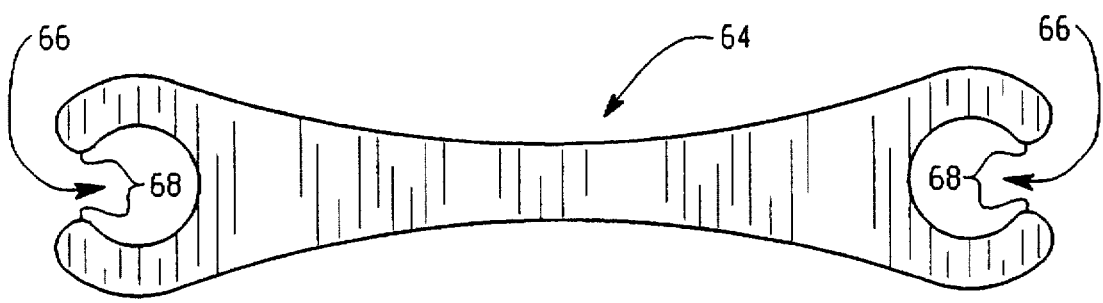
FIGS. 4A and 4B illustrate embodiments of a clip in accordance with the present invention.
Figure 4B:
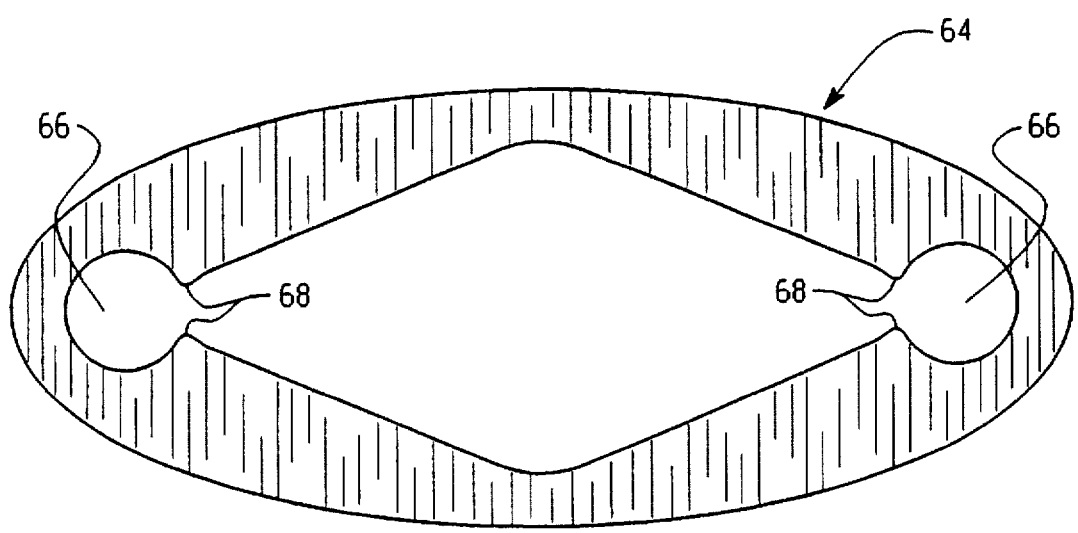
Figure 5:
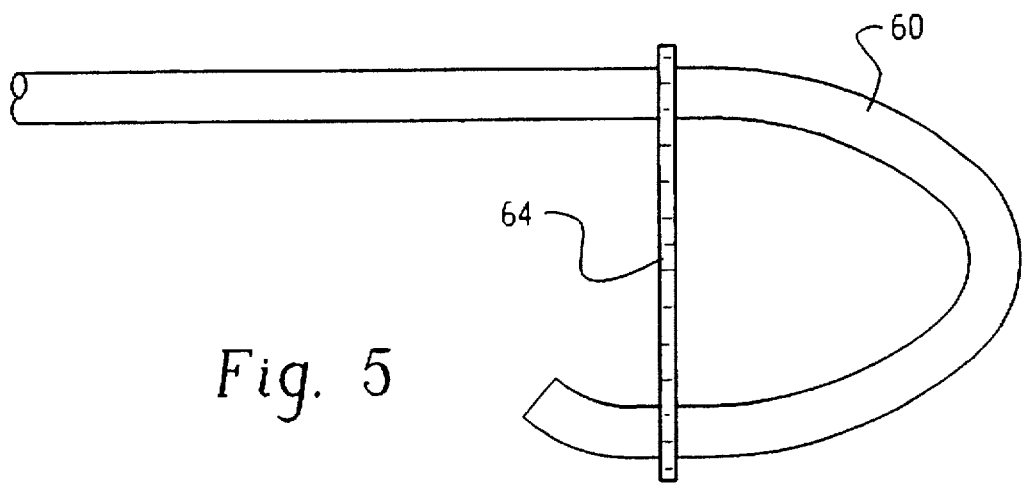
FIG. 5 is an illustration of the clip of FIG. 4A or 4B in use with a catheter in accordance with the present invention.

With reference to FIGS. 4A, 4B and 5, a reshaping clip 64 is configured to hold the catheter in its original shape 62A or to another preselected shape such as slightly more tightly folded or coiled. The clip 64 has enlarged holes 66 which are disposed at each end. To secure the clip 64 on the catheter 60, the catheter 60 is then snapped through the detents 68 defined at each side of the holes 66, frictionally securing the clip's position. The clip 64 has a sufficient resiliency that it is compressed to grip the catheter tightly even when forces are exerted on the catheter or clip that would urge the clip to slide or shift.

The clip 64 is fabricated from an open-cell porous material such as a rigid, open-cell polyethylene plastic material, ceramic material, sintered metal, or the like. In the illustrated embodiment, the clip has a distance between the centers of the holes 66 of about twenty-five millimeters with each hole 66 having a diameter of the frictionally engaged catheter. Of course, the length, width, diameter, number, and placement of holes 66, and other physical dimensions will change in accordance with the shape of the catheter or other plastic device.

During a decontamination cycle, the catheter 60 and attached clip 64 are placed within the reservoir tray 14 and are enveloped by a microbial decontamination fluid. The fluid is also channeled to a fitting 70 which is connected by a flexible tube 72 with the lumen of the catheter. The clip 64 has a sufficient porosity such that the microbial decontamination fluid penetrates through the porous clip 64 and contacts the surface of the catheter that is frictionally held in each hole 68. The porosity of the clip 64 assures microbial decontamination of that section in contact with the clip.

Again, the decontamination solution is heated to a temperature of about 5°–56° C. At this temperature, the catheter plastic softens allowing the plastic memory of the catheter to be reset in its original curve shape 62A. The porous clip 64 thus enables concurrent decontamination and reshaping of the catheter 60. Once the decontamination cycle is complete and the catheter 60 has sufficiently cooled, the clip 64 is removed. Of course, the decontaminant solution can be heated to other temperatures above the use temperature, typically about 37° C., and below the melt temperature of the plastic, preferably in the 40°–60° C. range. Other devices can also have their shape reset.

Figure 6:
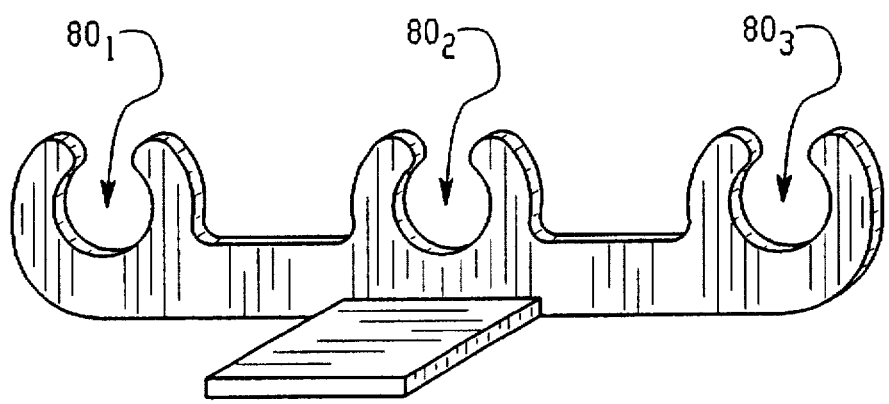
FIG. 6 is an alternative embodiment of a porous clip in accordance with the present invention.
Figure 7:
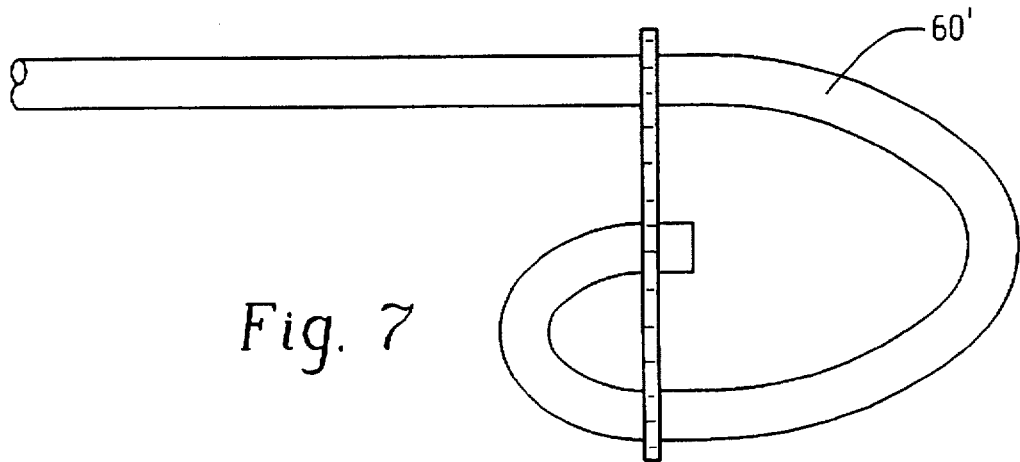
FIG. 7 is an illustration of the clip of FIG. 6 in use with a catheter.

Numerous other alternate embodiments will, of course, present themselves when the porous clip is adapted to catheters and structures of other shapes and configurations. For example, as illustrated in FIG. 6, the clip may have a plurality of catheter receiving pockets, such as pockets $80_1$, $80_2$, and $80_3$. Intermediate portions of the strip are again sufficiently dimensionally stable that the relative positions of the three pockets remain fixed when a spiral catheter 60' is inserted therein as illustrated in FIG. 7.

Figure 8:
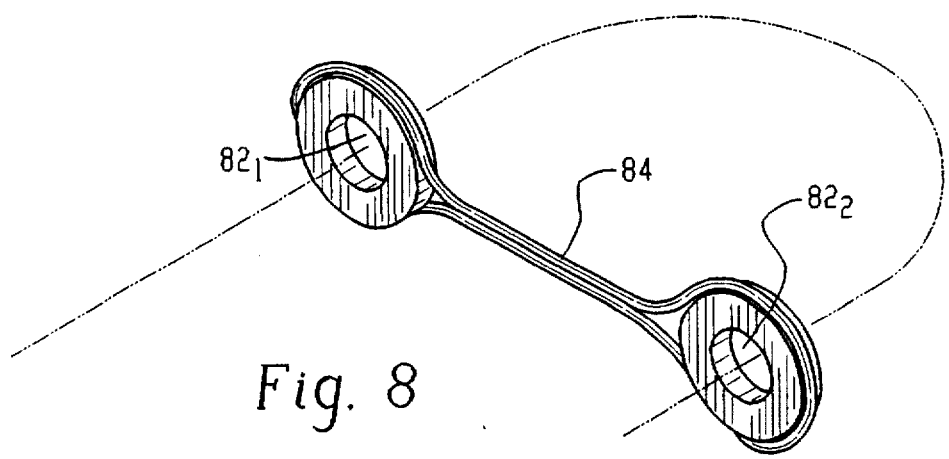
FIG. 8 is another alternate embodiment of a porous clip in accordance with the present invention.

In yet another alternate embodiment as illustrated in FIG. 8, portions of porous material $82_1$, and $82_2$ abut the catheter surface. The distance between the two porous portions is stably fixed by a section of flexible wire 84 or other constructions which fix the dimensional distance between the porous regions $82_1$ and $82_2$. Of course, additional porous portions may be connected in an analogous manner.

Figure 9:
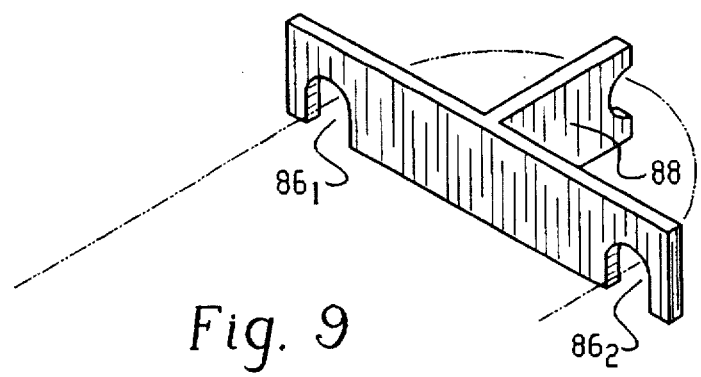
FIG. 9 is another alternate embodiment of the porous clip in accordance with the present invention.

In the embodiment of FIG. 9, the open-celled clip is configured to constrain a bent portion of the catheter to a preselected arc. The open-celled clip has catheter receiving regions $86_1$, and $86_2$. An extension or arc defining portion 88 extends upward from the clip to hold a curved portion of the catheter a preselected minimum diameter away. In this manner, the porous material is used to define three points which approximate a preselected arc. Of course, additional projections to the clip may be provided in order to approximate the preselected arc more precisely.

Figure 10:
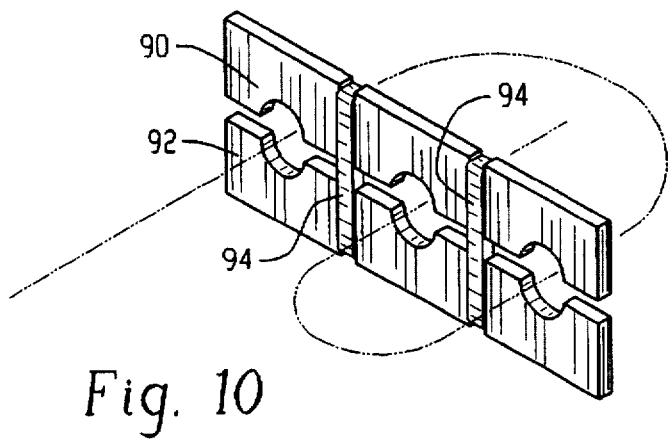
FIG. 10 is another alternate embodiment of a porous clip in accordance with the present invention.

With reference to FIG. 10, the clip includes an upper porous clip portion 90 and a lower porous clip portion 92. Clamps 94, such as elastomeric or spring bands, clamp the upper and lower portions together or against the catheter such that the position of the catheter is locked in place.

Figure 11:
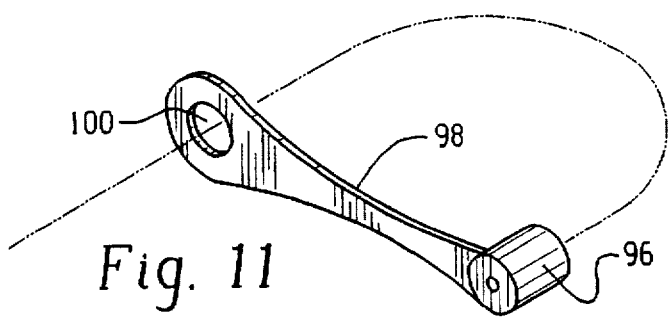
FIG. 11 is another alternate embodiment of a porous clip in accordance with the present invention.

In the embodiment of FIG. 11, a tubular cap or structure 96 or porous material extends over one end of the catheter. The porous cap is connected by a dimensionally stable section 98 to a construction, such as an aperture 100, for engaging another portion of the catheter or other heat setable device.

With reference again to FIG. 1, a plurality of porous clips 102 may be used to set the shape more precisely or to accommodate more complex shapes. The clips 102 can be connected to the tray 14. When connected to the tray, the clips may be U-shaped or have other configurations. Porous stops or guides 104 can also be mounted to the tray to assure accurate reshaping. Again, one end of the catheter can be connected to the flexible tubing 72 such that interior passages receive the anti-microbial fluid.

The invention has been described with reference to the preferred embodiment, obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of concurrently microbially decontaminating and reshaping a catheter with a shape memory which once had a first curve shape but now has a second curve shape, the method comprising:

placing at least one porous holding member into frictional contact with the catheter at selected surface points to retain the catheter in the first curve shape;

heating a microbial decontamination fluid to a temperature which resets the shape memory of the catheter;

immersing the catheter in the heated microbial decontamination fluid to decontaminate the catheter, the porous holding member having sufficient porosity such that the microbial decontamination fluid penetrates through the porous holding member to the selected surface points, concurrently assuring microbial decontamination of the catheter and resetting the shape memory of the catheter; and after cooling, removing the porous holding member portion from the catheter, the catheter being substantially reshaped into the first curve shape.

2. The method as set forth in claim 1 wherein the fluid is heated to at least 40° C.

3. The method as set forth in claim 1 wherein the fluid is heated to less than 60° C.

4. A microbial decontamination and instrument reshaping system comprising:

a reservoir for receiving an instrument to be microbially decontaminated and reshaped, the instrument being constructed of a material whose shape memory is reset at a first selected temperature;

a heater which heats an anti-microbial fluid to at least the first selected temperature;

at least one porous holding member for holding the instrument into a selected shape while the instrument is enveloped by the heated anti-microbial fluid, the porous holding member having a sufficient porosity that the anti-microbial fluid flows therethrough and contacts all surfaces of the instrument in contact with the porous holding member, and concurrently decontaminating and resetting the shape memory of the instrument such that the instrument retains the selected shape after cooling.

5. The system as set forth in claim 4 wherein the anti-microbial fluid includes an anti-microbial liquid solution and wherein the heater heats the anti-microbial liquid solution to a temperature below 60° C.

6. The system as set forth in claim 4 wherein the first selected temperature is above 40° C.

7. The system as set forth in claim 5 wherein the porous holding member has open regions for receiving the instrument therein.

8. The system as set forth in claim 7, wherein the porous holding member further includes detents adjacent the open regions to frictionally engage a portion of the instrument.

9. The system as set forth in claim 4 wherein the porous holding member defines an opening sized to receive a selected portion of the instrument in a frictional fit.

10. A microbial decontamination and instrument reshaping system comprising:

a reservoir for receiving an instrument to be microbially decontaminated and reshaped, the instrument being constructed of a material whose shape memory is reset at a first selected temperature;

a heater which heats an anti-microbial fluid to at least the first selected temperature; and at least one porous holding member constructed of a rigid open-celled material for holding the instrument in a selected shape while the instrument is enveloped by the heated anti-microbial fluid, the at least one holding member having a sufficient porosity that anti-microbial fluid flows therethrough and contacts all surfaces of the instrument in contact with the at least one holding member, and concurrently resetting the shape memory of the instrument such that the instrument retains the selected shape after cooling.

11. The system as set forth in claim 9 wherein the porous holding member has a second opening sized to receive a second selected portion of the instrument in a tight frictional engagement and a dimensionally stable portion connecting the first and second openings.

12. The system as set forth in claim 9 further including a means for interconnecting portions of the porous holding member that abut the instrument in a preselected spaced relationship such that the clip holds the instrument in a preselected curved configuration.

13. The system as set forth in claim 4 further including a pump which circulates the heated anti-microbial fluid from the heater through the reservoir.

14. A clip for resetting a shape memory of a curved item while the clip and the curved item are immersed in a decontamination fluid that is warmed to a temperature at which a shape memory of the item is reset, the clip comprising:

a first porous member portion for frictionally engaging the curved item;

a second porous member portion for frictionally engaging the curved item, the first and second porous member portions having sufficient porosity that the decontamination fluid flows therethrough to contact and decontaminate all surfaces of the curved item; and a dimensionally stable portion connecting the first and second porous member portions such that the clip holds the curved item in a selected flexed configuration while its shape memory is reset concurrently during decontamination.

15. The clip as set forth in claim 14 wherein the first porous member portion further includes an opening for receiving a portion of the curved item.

16. The clip as set forth in claim 15 wherein the first porous member portion defines at least one detent disposed adjacent the opening such that the selected portion of the item is snapped past the detent into the opening.

17. The clip as set forth in claim 16 wherein the second porous member portion has a second opening sized to receive a second portion of the curved item and at least a second detent adjacent the second opening such that the second portion of the item is snapped past the second detent into the second opening.

18. A clip for resetting a shape memory of an item while the clip and the item are immersed in a decontamination fluid that is warmed to a temperature at which a shape memory of the item is reset, the clip comprising:.

a first porous member portion constructed of an open-celled material for frictionally engaging the item;

a second porous member portion constructed of an open-celled material for frictionally engaging the item, the first and second porous member portions having sufficient porosity that the decontamination fluid flows therethrough to contact all surfaces of the item; and a dimensionally stable portion connecting the first and second porous member portions such that the clip holds the item in a selected flexed configuration while its shape memory is reset.

19. The clip as set forth in claim 18 wherein the open-celled material is rigid.

* * * * *